United States Patent
Koop et al.

(10) Patent No.: US 10,231,459 B2
(45) Date of Patent: Mar. 19, 2019

(54) PENFLUFEN AS A WOOD PRESERVATIVE AGAINST WOOD-DESTROYING BASIDIOMYCETES

(75) Inventors: Bernd Koop, Köln (DE); Martin Kugler, Leichlingen (DE); Thomas Jaetsch, Köln (DE); Johannes Kaulen, Odenthal (DE); Tanja Gerharz, Düsseldorf (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 13/880,619

(22) PCT Filed: Sep. 30, 2011

(86) PCT No.: PCT/EP2011/067163
§ 371 (c)(1),
(2), (4) Date: Dec. 5, 2013

(87) PCT Pub. No.: WO2012/055673
PCT Pub. Date: May 3, 2012

(65) Prior Publication Data
US 2014/0079806 A1    Mar. 20, 2014

(30) Foreign Application Priority Data

Oct. 25, 2010 (EP) .................................. 10188711
Nov. 4, 2010 (EP) .................................. 10190021

(51) Int. Cl.
| | | |
|---|---|---|
| *A01N 59/20* | (2006.01) | |
| *A01N 43/78* | (2006.01) | |
| *A01N 43/50* | (2006.01) | |
| *A01N 43/653* | (2006.01) | |
| *A01N 53/00* | (2006.01) | |
| *A01N 31/14* | (2006.01) | |
| *A01N 43/56* | (2006.01) | |
| *B27K 3/22* | (2006.01) | |
| *B27K 3/34* | (2006.01) | |
| *B27K 3/52* | (2006.01) | |
| *A01N 43/84* | (2006.01) | |

(52) U.S. Cl.
CPC ............. *A01N 59/20* (2013.01); *A01N 31/14* (2013.01); *A01N 43/50* (2013.01); *A01N 43/56* (2013.01); *A01N 43/653* (2013.01); *A01N 43/78* (2013.01); *A01N 43/84* (2013.01); *A01N 53/00* (2013.01); *B27K 3/22* (2013.01); *B27K 3/343* (2013.01); *B27K 3/52* (2013.01)

(58) Field of Classification Search
CPC ...................................................... A01N 59/20
See application file for complete search history.

(56) References Cited

U.S. PATENT DOCUMENTS

| | | | |
|---|---|---|---|
| 5,635,217 A * | 6/1997 | Goettsche et al. ............. 424/632 |
| 7,538,073 B2 | 5/2009 | Elbe et al. | |
| 8,747,908 B2 * | 6/2014 | Leach et al. .................. 424/630 |
| 2004/0204470 A1 | 10/2004 | Elbe et al. | |
| 2007/0276022 A1 | 11/2007 | Dunkel et al. | |
| 2008/0293566 A1 | 11/2008 | Suty-Heinze et al. | |
| 2009/0018015 A1 * | 1/2009 | Wachendorff-Neumann ............... A01N 37/22 504/100 |
| 2010/0016339 A1 | 1/2010 | Godwin et al. | |
| 2010/0029482 A1 * | 2/2010 | Benko et al. .................. 504/136 |
| 2010/0298139 A1 | 11/2010 | Suty-Heinze et al. | |
| 2011/0052555 A1 | 3/2011 | Coqueron et al. | |
| 2011/0098176 A1 | 4/2011 | Gewehr et al. | |
| 2011/0105579 A1 | 5/2011 | Wilhelm et al. | |
| 2011/0166020 A1 * | 7/2011 | Renner ................ C07D 403/12 504/100 |
| 2012/0004100 A1 * | 1/2012 | Hungenberg et al. ........ 504/100 |
| 2012/0021905 A1 | 1/2012 | Voeste et al. | |

FOREIGN PATENT DOCUMENTS

| | | | |
|---|---|---|---|
| WO | 2007110173 A2 | 10/2007 | |
| WO | WO2010028974 | * | 3/2010 |

OTHER PUBLICATIONS

Meros .Coniophora puteana. 2014 http://merops.sanger.ac.uk/cgi-bin/speccards?sp=sp028129;type=inhibitor;strain=4003.*
Schmidt. Wood and Tree Fungi Biology, Damage, Protection, and Use. 2006 http://dl.taq.ir/agriculture/wood_and_tree_fungi_schmidt.pdf.*
International Search Report from co-pending Application PCT/EP2011/067163 dated Feb. 23, 2012, 3 pages.
European Search Report from co-pending Application EP 10188711 dated Apr. 28, 2011, 2 pages.

* cited by examiner

*Primary Examiner* — Adam C Milligan
*Assistant Examiner* — Sarah Alawadi

(57) ABSTRACT

The invention relates to the use of penflufen for protecting wood and wood-comprising materials against wood-destroying basidiomycetes.

2 Claims, No Drawings

PENFLUFEN AS A WOOD PRESERVATIVE AGAINST WOOD-DESTROYING BASIDIOMYCETES

The invention relates to the use of penflufen for protecting wood and wood-comprising materials against wood-destroying basidiomycetes.

Penflufen (N-(2-[1,3-dimethylbutylphenyl]-5-fluoro-1,3-dimethyl-1H-pyrazole-4-carboxamide) is a pyrazolylcarboxanilide of the formula (I). In addition, penflufen is a fungicide.

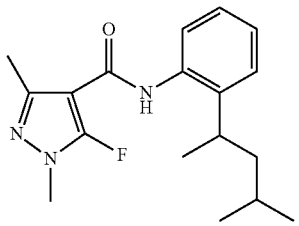

(I)

Pyrazolylcarboxanilides are specific carboxamides and are known from WO 03/010149 for controlling unwanted microorganisms in crop protection and in the protection of materials. WO 03/010149 mentions penflufen in a list of further pyrazolylcarboxanilides, and the action of penflufen as a crop protection agent is shown in one example.

The use of optically active carboxamides, also in mixtures with other biocidal compounds, for crop protection and the protection of materials is known from WO 2005/058839. The action of an optically active enantiomer of penflufen for crop protection is shown in the examples.

WO 2006/114212 discloses active compound combinations of carboxamides with known insecticidally active compounds for controlling unwanted animal pests and also unwanted phytopathogenic fungi, also for use in crop protection. Mixtures of penflufen and insecticides have also been described. The examples show, inter alia, the efficacy of penflufen in mixtures with other compounds in crop protection.

Synergistic fungicidal active compound combinations comprising carboxamides with a wide variety of different mixing partners are known from WO 2005/041653. Here, too, penflufen is, among others, mentioned as a mixing partner. The use described of the synergistic fungicidal active compound combinations is the control of phytopathogenic fungi.

Furthermore, from WO2009/098218 and WO2009/090181 it is known to use carboxamides for crop protection and for the protection of materials.

Further active compound combinations which may, among others, also comprise penflufen are known from WO 2007/110173 and WO 2008/014955.

The current active compounds and active compound combinations have the disadvantage that they frequently do not have comparably high activities against different genera of wood-destroying basidiomycetes in wood preservation.

Accordingly, it is an object of the present invention to provide active compounds having a relatively broad action, which compounds can be employed efficiently for the preservation of wood and wood-comprising materials against wood-destroying basidiomycetes.

Surprisingly, it has been found that penflufen as active compound has a particularly high and broad activity against wood-destroying basidiomycetes. Even compared to the structurally only slightly different compounds (II) and (III) known from WO 03/010149, penflufen has a very high activity against different genera of wood-destroying basidiomycetes.

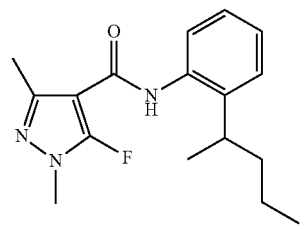

(II)

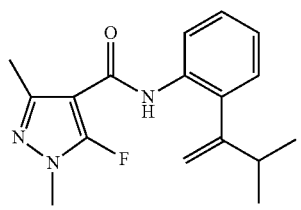

(III)

Accordingly, the invention provides the use of penflufen for protecting wood and wood-comprising materials against wood-destroying basidiomycetes.

Penflufen may be employed as a racemate, in enantiomerically pure form or as an enriched enantiomer mixture. A use as salt or acid addition compound is also possible, salts being understood as meaning in particular sodium, potassium, magnesium, calcium, zinc, aluminium, iron and copper salts, and acid addition compounds being understood as meaning in particular adducts with hydrohalic acids, for example hydrogen chloride and hydrogen bromide, carboxylic acids such as, for example, formic acid, acetic acid, tartaric acid and oxalic acid, sulphonic acids such as, for example, p-toluenesulphonic acid, and also sulphuric acid, phosphoric acid and nitric acid.

Wood is to be understood as meaning, in particular: construction timber, wooden beams, railway sleepers, bridge components, jetties, vehicles made of wood, boxes, pallets, containers, telephone poles, wooden fences, wood lagging, windows and doors made of wood, joiners work and wood-based materials used in domestic construction or carpentry and joinery.

Wood-comprising materials are to be understood as meaning, in particular, timber products or wood/plastic composites (WPC).

Timber products are to be understood as meaning, in particular: plywood, chipboard, fibre board, oriented strand board (OSB) or composite board.

Wood/plastic composite is to be understood as meaning, in particular: thermoplastically processable composites consisting of wood, plastic and additives.

Wood is particularly preferred.

For the purposes of the present invention, particular preference is given to the preservation of wood.

By way of example and by way of preference, the following may be mentioned as wood-destroying basidiomycetes capable of effecting degradation or modification of wood and wood-comprising materials:

*Coniophora* such as *Coniophora puteana*,
*Lentinus* such as *Lentinus tigrinus*,
*Polyporus* such as *Polyporus versicolor*,

*Gloeophyllum*, such as *Gloeophyllum trabeum*,
*Poria*, such as *Poria placenta*,
*Stereum*, such as *Stereum sanguinolentum*.

Particular preference is given to wood-destroying basidiomycetes, especially holobasidiomycetes. Wood-destroying basidiomycetes and holobasidiomycetes are fungi.

Very particularly preferably, penflufen or/and the compositions according to the invention act against species of the genera *Gloeophyllum, Coniophora, Coriolus, Stereum* or *Poria*. Even more preferably, penflufen or/and the compositions according to the invention act against species of the genera *Coniphora* or *Poria*, in particular against *Poria placenta* and *Coniphora puteana*. Even more preference is given to the use of penflufen for protecting wood against *Poria placenta*.

Penflufen may be employed in the customary formulations, such as solutions, emulsions, suspensions, powders, foams, pastes, granules, aerosoles and very fine encapsulations in polymeric substances.

Such formulations for preserving wood and wood-destroying materials are produced in a known manner, for example by mixing the active compound with extenders, that is, liquid solvents, liquefied gases under pressure, and/or solid carriers, optionally with the use of surfactants, that is emulsifiers and/or dispersants, and/or foam-formers. If the extender used is water, it is also possible to use, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycerol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks. Suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulfonates, alkylsulfates, arylsulfonates and protein hydrolysates. Suitable dispersants are: for example lignosulfite waste liquors and methylcellulose.

Tackifiers, such as carboxymethyl cellulose, natural and synthetic polymers in the form of powders, granules or latices, such as gum arabic, polyvinyl alcohol and polyvinyl acetate, and also natural phospholipids, such as cephalins and lecithins, and synthetic phospholipids can additionally be used in the formulations. Further additives may be mineral and vegetable oils.

It is furthermore possible to use colorants such as inorganic pigments, for example iron oxide, titanium oxide, Prussian Blue, copper oxide and organic dyes, such as alizarine, azo and metallophthalocyanine dyes.

The formulations generally comprise from 0.1 to 95% by weight of active compound, preferably between 0.5 and 90% by weight.

Surprisingly, it has now been found that the active compound combinations below have synergistic activity, i.e. the efficacy of the active compound combinations is greater than the sum of the efficacies of the individual active compounds. Accordingly, they are particularly suitable for being employed for protecting wood and wood-comprising materials against wood-destroying basidiomycetes:

Preference is given to mixtures of penflufen with copper compounds such as, for example, bis-(N-cyclohexyldiazeniumdioxy)copper (Cu-HDO), copper(I) oxide, copper(II) oxide, copper carbonate, copper sulphate, copper chloride, copper borate, copper citrate, copper salt of 8-hydroxyquinoline, copper naphthenate. Particular preference is given to mixtures with copper(I) oxide and/or copper(II) oxide.

Preference is given to mixtures of penflufen with sulphenamides such as dichlofluanid, tolylfluanid, folpet, fluorfolpet, captan and captofol.

Preference is given to mixtures of penflufen with imidazoles such as, for example, clotrimazole, bifonazole, climbazole, econazole, fenapanil, imazalil, isoconazole, ketoconazole, lombazole, miconazole, pefurazoate, prochloraz, triflumizole and their metal salts and acid adducts. Particular preference is given to mixtures with prochloraz and also its metal salts and acid adducts.

Preference is given to mixtures of penflufen with benzimidazoles such as carbendazim, benomyl, fuberidazole, thiabendazole or salts thereof. Particular preference is given to the mixture with thiabendazole.

Preference is given to mixtures of penflufen with morpholine derivatives such as, for example, aldimorph, dimethomorph, dodemorph, falimorph, fenpropidin fenpropimorph, tridemorph, trimorphamid and their arylsulphonate salts such as, for example, p-toluenesulphonic acid and p-dodecylphenylsulphonic acid. Particular preference is given to the mixture with fenpropimorph.

Preference is given to mixtures of penflufen with pyrethroids such as, for example, permethrin, cypermethrin, bifenthrin, cyfluthrin, deltamethrin, prallethrin, fenvalerate, allethrin and etofenprox. Particular preference is given to mixtures with cypermethrin, permethrin, bifenthrin and etofenprox.

Accordingly, the invention also embraces compositions comprising penflufen and at least one further compound from the group consisting of copper oxide and thiabendazole.

Moreover, the invention embraces wood and wood-comprising materials treated with at least one composition comprising penflufen and at least one further compound from the group consisting of copper oxide and thiabendazole.

Moreover, it has in particular been found, surprisingly, that, when the composition comprises fenpropimorph in addition to penflufen, a particularly high synergistic activity is found when the composition comprises 75-85% by weight of fenpropimorph and 15-25% by weight of penflufen.

A particularly high synergistic activity has furthermore been found for the mixture comprising penflufen and a further compound from the group consisting of copper oxide and thiabendazole after impregnation of the wood and the timber products on these materials themselves.

Penflufen can be used as such or in formulations, where it can be employed as only biocide without any other active compounds or in combination with known fungicides, bactericides or insecticides, for example to broaden the activity spectrum or to prevent the development of resistance.

Particularly favourable co-components in mixtures are, for example, the following compounds:

triazoles such as:
azaconazole, bitertanol, bromuconazole, cyproconazole, diclobutrazol, difenoconazole, diniconazole, epoxyconazole, etaconazole, fenbuconazole, fluquinconazole, flusilazole, flutriafol, furconazole, hexaconazole, imibenconazole, ipconazole, myclobutanil, metconazole, penconazole, propiconazole, prothioconazole, simeconazole, tebuconazole, tetraconazole, triadimefon, triadimenol, triticonazole and uniconazole and their metal salts and acid adducts;

imidazoles such as:
clotrimazole, bifonazole, climbazole, econazole, fenapanil, imazalil, isoconazole, ketoconazole, lombazole, miconazole, pefurazoate, prochloraz, triflumizole and their metal salts and acid adducts;

pyridines and pyrimidines such as:
ancymidol, buthiobate, fenarimol, mepanipyrin, nuarimol, pyroxyfur, triamirol;

succinate dehydrogenase inhibitors such as:
benodanil, bixafen, boscalid, carboxim, carboxim sulphoxide, cyclafluramid, fenfuram, flutanil, furametpyr, furcarbanil, furmecyclox, mebenil, mepronil, methfuroxam, metsulfovax, nicobifen, pyrocarbolid, oxycarboxin, Suirlan, Seedvax;

naphthalene derivatives such as:
terbinafine, naftifine, butenafine, 3-chloro-7-(2-aza-2,7,7-trimethyl-oct-3-en-5-ine);

sulphenamides such as:
dichlofluanid, tolylfluanid, folpet, fluorofolpet, captan, captofol;

benzimidazoles such as:
carbendazim, benomyl, fuberidazole, thiabendazole or their salts;

morpholine derivatives such as:
aldimorph, dimethomorph, dodemorph, falimorph, fenpropidin fenpropimorph, tridemorph, trimorphamid and their arylsulphonate salts such as, for example, p-toluenesulphonic acid and p-dodecylphenyl-sulphonic acid;

benzothiazoles such as:
2-mercaptobenzothiazole;

benzothiophene dioxides such as:
N-cyclohexyl-benzo[b]thiophene carboxamide S,S-dioxide;

benzamides such as:
2,6-dichloro-N-(4-trifluoromethylbenzyl)-benzamide, tecloftalam;

boron compounds such as:
boric acid, boric ester, borax;

formaldehyde and formaldehyde-releasing compounds such as:
benzyl alcohol mono-(poly)-hemiformal, n-butanol hemiformal, dazomet, ethylene glycol hemiformal, hexa-hydro-S-triazine, hexamethylenetetramine, N-hydroxymethyl-N'-methylthiourea, N-methylolchloroacetamide, oxazolidine, paraformaldehyde, taurolin, tetrahydro-1,3-oxazine, N-(2-hydroxypropyl)-amine-methanol, tetramethylol acetylenediurea;

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octyl-isothiazolin-3-one, 4,5-trimethylene-isothiazolinone, 4,5-benzisothiazolinone;

aldehydes such as:
cinnamaldehyde, formaldehyde, glutardialdehyde, β-bromocinnamaldehyde, o-phthaldialdehyde;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzyldimethyldodecylammonium chloride, dichlorobenzyl-dimethyl-alkyl-ammonium chloride, didecyldimethylammonium chloride, dioctyl-dimethyl-ammonium chloride, N-hexadecyl-trimethyl-ammonium chloride, 1-hexadecyl-pyridinium chloride, iminoctadine tris(albesilate);

iodine derivatives such as:
diiodomethyl p-tolyl sulphone, 3-iodo-2-propynyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;

phenols such as:
tribromophenol, tetrachlorophenol, 3-methyl-4-chlorophenol, 3,5-dimethyl-4-chlorophenol, dichlorophen, 2-benzyl-4-chlorophenol, triclosan, diclosan, hexachlorophene, p-hydroxybenzoic esters, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and their alkali and alkaline earth metal salts;

microbicides with an activated halogen group such as:
bronopol, bronidox, 2-bromo-2-nitro-1,3-propanediol, 2-bromo-4'-hydroxy-acetophenone, 1-bromo-3-chloro-4,4,5,5-tetramethyl-2-imidazolidinone, β-bromo-β-nitrostyrene, chloracetamid, chloramin T, 1,3-dibromo-4,4,5,5-tetramethyl-2-imidazolidinone, dichloramin T, 3,4-dichloro-(3H)-1,2-dithiol-3-one, 2,2-dibromo-3-nitrile-propionamide, 1,2-dibromo-2,4-dicyanobutane, halane, halazone, mucochloric acid, phenyl(2chlorocyano-vinyl)sulphone, phenyl(1,2-dichloro-2-cyanovinyl)sulphone, trichloroisocyanuric acid;

pyridines such as:
1-hydroxy-2-pyridinethione (and their Cu, Na, Fe, Mn, Zn salts), tetrachloro-4-methylsulphonylpyridine, pyrimethanol, mepanipyrim, dipyrithione, 1-hydroxy-4-methyl-6-(2,4,4-trimethylpentyl)-2(1H)-pyridine;

methoxyacrylates or similar such as:
azoxystrobin, dimoxystrobin, fluoxastrobin, kresoximmethyl, metominostrobin, orysastrobin, picoxystrobin, pyraclostrobin, trifloxystrobin;

metal soaps such as:
salts of the metals tin, copper and zinc with higher fatty acids, resin acids, naphthenoic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:
salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate;

oxides such as:
oxides of the metals tin, copper and zinc, such as, for example, tributyltin oxide, $Cu_2O$, CuO, ZnO;
oxidizing agents such as:
hydrogen peroxide, peracetic acid, potassium persulphate;
dithiocarbamates such as:
cufraneb, ferban, potassium N-hydroxymethyl-N'-methyl-dithiocarbamate, sodium dimethyldithiocarbamate, potassium dimethyldithiocarbamate, mancozeb, maneb, metam, metiram, thiram, zineb, ziram;
nitriles such as:
2,4,5,6-tetrachloroisophthalonitrile, disodium cyano-dithioimidocarbamate;
quinolines such as:
8-hydroxyquinoline and its copper salts;
other fungicides and bactericides such as:
bethozaxin, 5-hydroxy-2(5H)furanone, 4,5-benzodithiazolinone, 4,5-trimethylenedithiazolinone, N-(2-p-chlorobenzoylethyl)hexaminium chloride, 2-oxo-2-(4-hydroxyphenyl)acetohydroxycinnamoyl chloride, tris-N-(cyclohexyldiazeniumdioxy)aluminium, N-(cyclohexyldiazeniumdioxy)tributyltin or its potassium salts, bis-N-(cyclohexyldiazeniumdioxy)copper, iprovalicarb, fenhexamide, spiroxamine, carpropamid, diflumetorin, quinoxyfen, famoxadone, polyoxorim, acibenzolar S-methyl, furametpyr, thifluzamide, metalaxyl-M, benthiavalicarb, metrafenone, cyflufenamid, tiadinil, tea tree oil, phenoxyethanol,
Ag—, Zn— or Cu—containing zeolites alone or incorporated into polymeric materials.

Insecticides:
abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtin, azinphos A, azinphos M, azocyclotin,
*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrifluron, bromophos A, bromophos M, bufencarb, buprofezin, butathiophos, butocarboxim, butoxycarboxim,
cadusafos, carbaryl, carbofuran, carbophenothion, carbosulfan, cartap, chinomethionat, cloethocarb, 4-chloro-2-(2-chloro-2-methylpropyl)-5-[(6-iodo-3-pyridinyl)methoxy]-3(2H)-pyridazinone (CAS-RN: 120955-77-3), chlordane, chlorethoxyfos, chlorfenapyr, chlorfenvinphos, chlorfluazuron, chlormephos, N-[(6-chloro-3-pyridinyl)methyl]-N'-cyano-N-methylethaneimidamide, chlorpicrin, chlorpyrifos A, chlorpyrifos M, cis-resmethrin, clocythrin, clothiazoben, cypophenothrin, clofentezin, coumaphos, cyanophos, cycloprothrin, cyfluthrin, cyhalothrin, cyhexatin, cypermethrin, cyromazin,
decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl(4-ethoxyphenyl)silylmethyl-3-phenoxybenzyl ether, dimethylvinphos, dioxathion, disulfoton,
eflusilanate, emamectin, empenthrin, endosulfan, O-ethyl O-(4-nitrophenyl) P-phenylphosphonothioate, esfenvalerate, ethiofencarb, ethion, etofenprox, etrimphos, etoxazole, etobenzanid,
fenamiphos, fenazaquin, fenbutatin oxide, fenfluthrin, fenitrothion, fenobucarb, fenothiocarb, fenoxycarb, fenpropathrin, fenpyrad, fenpyroximate, fensulfothion, fenthion,
fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan, fosthiazate, fubfenprox, furathiocarb
halofenocid, HCH (CAS RN: 58-89-9), heptenophos, hexaflumuron, hexythiazox, hydramethylnon, hydroprene,
imidacloprid, imiprothrin, indoxycarb, iodfenfos, iprinomectin, iprobenfos, isazophos, isoamidophos, isofenphos, isoprocarb, isoprothiolane, isoxathion, ivermectin,
kadedrin,
lambda-cyhalothrin, lufenuron,
malathion, mecarbam, mervinphos, mesulfenphos, metaldehyde, methacrifos, methamidophos, methidathion, methiocarb, methomyl, metalcarb, milbemectin, monocrotophos, moxiectin,
naled, nicotine, nitenpyram, noviflumuron,
omethoate, oxamyl, oxydemethon M, oxydeprofos,
parathion A, parathion M, penfluron, permethrin, 2-(4-phenoxyphenoxy)-ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium,
quinalphos,
resmethrin, rotenone,
salithion, sebufos, silafluofen, spinosad, spirodiclofen, spiromesifen, sulfotep, sulprofos,
tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron, trichlorfon, triflumuron, trimethacarb,
vamidothion, xylylcarb, zetamethrin;

herbicides and algicides:
acetochlor, acifluorfen, aclonifen, acrolein, alachlor, alloxydim, ametryn, amidosulfuron, amitrole, ammonium sulphamate, anilofos, asulam, atrazine, azafenidin, aziptrotryne, azimsulfuron,
benazolin, benfluralin, benfuresate, bensulfuron, bensulphide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim,
carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulfuron, chlorthal, chlorthiamid, cinmethylin, cinofulsuron, clefoxydim, clethodim, clomazone, chlomeprop, clopyralid, cyanamide, cyanazine, cybutryn, cycloate, cycloxydim, chloroxynil, clodinafop-propargyl, cumyluron, clometoxyfen, cyhalofop, cyhalofop-butyl, clopyrasuluron, cyclosulfamuron,
diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diuron, DNOC (2-4,6-dinitrophenol), DSMA (disodium methylarsonate), (2,4-dichlorophenoxy)acetic acid, daimuron, dalapon, dazomet, 2,4-DB (4-(2,4-dichlorophenoxy)butanoic acid), desmedipham, desmetryn, dicamba, dichlobenil, dimethamid, dithiopyr, dimethametryn, eglinazine, endothal, EPTC (S-ethyl dipropylthiocarbamate), esprocarb, ethalfluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluoroglycofen, fluoronitrofen, flupropanate, flurenol, fluridone, flurochloridone, fluroxypyr, fomesafen, fosamine, fosametine, flamprop-isopropyl, flamprop-isopropyl-L, flufenpyr, flumiclorac-pentyl, flumipropyn, flumioxzim, flurtamone, flumioxzim, flupyrsulfuron-methyl, fluthiacet-methyl, glyphosate, glufosinate-ammonium, haloxyfop, hexazinone, imazamethabenz, isoproturon, isoxaben, isoxapyrifop, imazapyr, imazaquin, imazethapyr, ioxynil, isopropalin, imazosulfuron, imazomox, isoxaflutole, imazapic, ketospiradox, lactofen, lenacil, linuron, MCPA (2-(4-chloro-2-methylphenoxy)acetic acid), MCPA-hydrazide, MCPA-thioethyl, MCPB (4-(4-chloro-2-methylphenoxy)butanoic acid), mecoprop, mecoprop-P, mefenacet, mefluidide, mesosulfuron, metam, metamifop, metamitron, metazachlor, methabenzthiazuron, methazole, methoroptryne, methyldymron, methyl isothiocyanate, metobromuron, metoxuron, metribuzin, metsulfuron, molinate, monalide, monalinuron, MSMA (monosodium methyl arsonate), metolachlor, metosulam, metobenzuron, naproanilide, napropamide, naptalam, neburon, nicosulfuron, norflurazon, sodium chloride, oxadiazon, oxyfluorfen, oxysulfuron, orbencarb, oryzalin, oxadiargyl, propyzamide, prosulphocarb, pyrazolate, pyrazolsulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulfuron, prodiamine, profoxydim, prometryn, propachlor, propanil, propaquizafob, propazine, propham, propisochlor, pyriminobacmethyl, pelargonic acid, pyrithiobac, pyraflufen-ethyl, quinmerac, quinocloamine, quizalofop, quizalofop-P, quinchlorac, rimsulfuron, sethoxydim, sifuron, simazine, simetryn, sulfosulfuron, sulfometuron, sulfentrazone, sulcotrione, sulfosate, tar oils, TCA (trichloroacetic acid), TCA-sodium, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluralin, tycor, thidiazimin, thiazopyr, triflusulfuron, vernolate.

Preferred co-components in mixtures of penflufen are those having synergistic efficacy.

The use concentrations of the active compounds according to the invention depend on the type and the occurrence of the wood-destroying basidiomycetes to be controlled, and on the composition of the material to be preserved. The optimal rate of use can be determined by test series. In general, the use concentrations are in the range from 0.001 to 5% by weight, preferably from 0.005 to 1.0% by weight of active compound, based on the material to be preserved.

The invention relates in particular to a process for the preservation of wood and wood-comprising materials, characterized in that the wood or the wood-comprising material is treated with penflufen and at least one diluent or solvent, optionally further auxiliaries and additives and optionally one or more active compounds, by painting, spraying, drenching, submersion, impregnation or in any other manner. Preference is given to industrial impregnation processes such as the vacuum, double vacuum, vacuum-pressure or pressure process.

There is a large number of processes for treating wood and wood-comprising materials with preservatives. The processes below can be used in accordance with the invention; however, there are further processes practically employed.

Painting is a preferred process for applying the wood preservative. In most cases, a plurality of process steps are required to achieve the loading required. Both water- and solvent-based wood preservatives may be employed. Retention, i. e. the amount of wood preservative taken up by the wood, is preferably 60-200 $g/m^2$. By atomizing and spraying, it is possible to achieve penetration depths and retentions similar to painting.

In the case of submersion, the wood is preferably submersed completely in the wood preservative in a bath for a few seconds to minutes. The uptake of the preservative depends inter alia on the concentration and the submersion time. The penetration depths achieved on submersion correspond roughly to those achieved when painting. The achievable wood preservative retentions are preferably about 100-500 $g/m^2$. Trough drenching is a special submersion process. Here, wood is submerged preferably for a period of several hours to days, which allows uniform and deep penetration to be achieved.

In industrial wood preservation, preference is given to using pressure processes to obtain a relatively uniform and deep distribution of the protection agent. In cylinder pressure impregnation, the wood is treated in a cylinder-shaped cell. Depending on the type of wood, the intended purpose, the moistness of the wood, the wood preservative used and the desired penetration depth, various processes are employed. The best protection is achieved in the full-cell process. Here, first, a vacuum is applied and the wood preservative is then pressed into the wood under high pressure. In this manner, it is possible to achieve very high uptake rates; the wood preservative retention is about 200-700 $kg/m^3$.

The empty-cell process (for example the Lowry process) is preferably used for types of wood that are easily impregnated. In this process, preferably, no pre-vacuum is applied, and the preservative solution is immediately pressed into the wood under superatmospheric pressure. After the pressure phase, owing to the compressed air, some of the wood preservative is pressed out of the wood again. The achievable retention is generally smaller than in the full-cell process.

The alternating pressure process is preferably employed to drench wood having a moistness of more than 80%. Here, the cell is flooded without pre-vacuum with the wood preservative. Following a pre-pressure phase of about 30-60 min, the pressure is changed dynamically. Preferably, vacuum and pressure phases alternate within short intervals.

The double vacuum process is preferably employed for impregnating dry wood. Here, the cell is preferably evacuated in a first step, and the cell is then flooded with the wood preservative and the wood is drenched at atmospheric pressure. Subsequently, vacuum is then re-applied to remove excess solution. Both solvent- and water-based wood preservatives may be employed. In this process, the retention of wood preservative is preferably 20-40 $kg/m^3$.

Wood/plastic composites protected with penflufen can be prepared, for example, by mixing, in particular extruding or spray-moulding, wood particles, a thermoplastic polymer and penflufen, if appropriate in the form of a formulation, and optionally formulation auxiliaries with input of thermal energy.

Wood composites can be treated, for example, by the glue incorporation method. Here, penflufen, if appropriate in the form of a formulation, is added to the glue liquor and this biocidally finished glue is applied in a customary manner to the chips, in particular applied using a nozzle (for example in the case of chip boards or OSB boards) or applied via rollers to the veneer (for example in the case of plywood). In the surface process, the penflufen, if appropriate in the form of a formulation, is sprayed to the timber product or applied using a roll.

In a manner according to the invention, by using penflufen in wood preservation, it is possible to protect wood and wood-containing materials effectively against wood-destroying basidiomycetes. Here, penflufen meets the high requirements with respect to stability, leaching behaviour, colour and compatibility with very different formulation auxiliaries in spite of the sometimes extreme conditions caused by the use of drastic application processes, which, frequently, are not met by active compounds which preferably act against phytopathogenic fungi. These properties are enhanced even more in the mixtures according to the invention, by virtue of synergistic actions.

EXAMPLES

Example 1

Inhibition Test with Giant Colonies of Wood-destroying Basidiomycetes

Mycelium pieces were punched out of colonies of *Coniophora puteana, Poria placenta, Lentinus tigrinus, Coriolus versicolor* and *Gloeophyllum trabeum* and incubated on an agar nutrient soil at 26° C. The inhibition of the growth of the hyphae on active compound-comprising nutrient soil was compared to the longitudinal growth without addition of active compound and rated as inhibition in percent (incubation time: about 1 week, depending on the fungal growth of the comparative sample without active compound). The active compound concentration was 1 ppm.

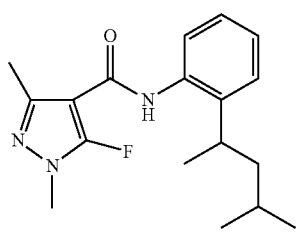 [SMILES: Cc1nn(C)c(F)c1C(=O)Nc1ccccc1C(C)CC(C)C]

(I)

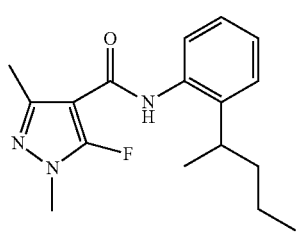 [SMILES: CCCC(C)c1ccccc1NC(=O)c1c(C)nn(C)c1F]

(II)

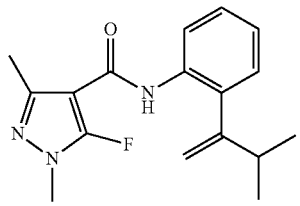 [SMILES: C=C(c1ccccc1NC(=O)c1c(C)nn(C)c1F)C(C)C]

(III)

|  |  | Inhibition [%] | | |
| --- | --- | --- | --- | --- |
| No. | Fungus | I | II | III |
| 1 | Coniophora puteana | 100 | 12 | 25 |
| 2 | Coriolus versicolor | 100 | 15 | 78 |
| 3 | Lentinus tigrinus | 100 | 17 | 37 |
| 4 | Poria placenta | 100 | 3 | 45 |
| 5 | Gloeophyllum trabeum | 100 | 11 | 18 |

Penflufen (I) acts markedly better against wood-destroying basidiomycetes than (II) and (III).

Example 2

Synergism Tests

Mycelium pieces were punched out of a colony of the wood-destroying fungus in question and incubated on a malt extract/peptone-containing nutrient agar at 26° C. The growth of the hyphae with and without active compound was compared. The minimum inhibitory concentration (MIC) stated was the concentration at which the radial hyphae growth was suppressed completely.

The synergism was determined using the method described by Kull et al. (F. C. Kull, P. C. Eismann, H. D. Sylvestrowicz, R. L. Mayer, Applied Microbiology 1961, 9, 538-541). The following relationships apply:

$$\frac{Q_A}{Q_a} + \frac{Q_B}{Q_b} = SI$$

SI=1 means additivity
SI>1 means antagonism
SI<1 means synergism
$Q_a$=concentration of substance A which is the MIC
$Q_b$=concentration of substance B which is the MIC
$Q_A$=concentration of substance A in the concentration of A/B at which microbial growth is suppressed
$Q_B$=concentration of substance A in the concentration of A/B at which microbial growth is suppressed 2.1 Combinations of Penflufen and Thiabendazole against the Wood-destroying Organism *Coriolus versicolor*

|  | MIC against *Coriolus versicolor* (ppm) | SI |
| --- | --- | --- |
| penflufen | 0.3 | — |
| penflufen:thiabendazole 9:1 | 0.3 | 0.91 |
| penflufen:thiabendazole 3:2 | 0.3 | 0.64 |
| penflufen:thiabendazole 1:1 | 0.5 | 0.92 |
| penflufen:thiabendazole 2:3 | 0.5 | 0.77 |
| thiabendazole | 3.0 | — |

2.2 Combinations of Penflufen and Fenpropimorph against the Wood-destroying Organisms *Coniophora puteana* and *Lentinus tigrinus*

|  |  | MIC (ppm) | | SI | |
|---|---|---|---|---|---|
|  |  | Coniophora puteana | Lentinus tigrinus | Coniophora puteana | Lentinus tigrinus |
| penflufen |  | 1.0 | 0.5 |  |  |
| penflufen:fenpropimorph | 7:3 | 0.7 | 0.5 | 0.50 | 0.71 |
| penflufen:fenpropimorph | 6:4 | 1.0 | 0.5 | 0.61 | 0.61 |
| penflufen:fenpropimorph | 1:1 | 0.7 | 0.7 | 0.36 | 0.71 |
| penflufen:fenpropimorph | 4:6 | 0.7 | 0.7 | 0.29 | 0.57 |
| penflufen:fenpropimorph | 3:7 | 0.7 | 0.7 | 0.23 | 0.44 |
| penflufen:fenpropimorph | 2:8 | 0.5 | 0.5 | 0.11 | 0.21 |
| penflufen:fenpropimorph | 1:9 | 0.7 | 3.0 | 0.09 | 0.69 |
| fenpropimorph |  | 30 | 30 |  |  |

2.3 Combinations of Penflufen and Copper(II) Oxide against the Wood-destroying Organism *Gloeophyllum trabeum*

|  | MIC against Gloeophyllum trabeum (ppm) | SI |
|---|---|---|
| penflufen | 0.3 | — |
| penflufen:copper(II) oxide 7:3 | 0.3 | 0.70 |
| penflufen:copper(II) oxide 6:4 | 0.1 | 0.20 |
| penflufen:copper(II) oxide 1:1 | 0.3 | 0.50 |
| penflufen:copper(II) oxide 4:6 | 0.5 | 0.67 |
| penflufen:copper(II) oxide 3:7 | 0.5 | 0.50 |
| penflufen:copper(II) oxide 2:8 | 1.0 | 0.67 |
| copper(II) oxide | 100.0 | — |

2.4 Combinations of Penflufen and Tebuconazole against the Wood-destroying Organism *Stereum sanguinolentum*

|  | MIC against Stereum sanguinolentum (ppm) | SI |
|---|---|---|
| penflufen | 3.0 | — |
| penflufen:tebuconazole 6:4 | 1.0 | 0.27 |
| penflufen:tebuconazole 1:1 | 3.0 | 0.75 |
| penflufen:tebuconazole 4:6 | 0.7 | 0.16 |
| penflufen:tebuconazole 3:7 | 0.5 | 0.11 |
| penflufen:tebuconazole 2:8 | 0.5 | 0.10 |
| penflufen:tebuconazole 1:9 | 1.0 | 0.18 |
| tebuconazole | 6.0 | — |

2.5 Combinations of Penflufen and Propiconazole against the Wood-destroying Organism *Coniophora puteana*

|  | MIC against Coniophora puteana (ppm) | SI |
|---|---|---|
| penflufen | 3.0 | — |
| penflufen:propiconazole 9:1 | 1.0 | 0.33 |
| penflufen:propiconazole 8:2 | 0.5 | 0.17 |
| penflufen:propiconazole 7:3 | 0.5 | 0.17 |
| penflufen:propiconazole 6:4 | 0.5 | 0.17 |
| penflufen:propiconazole 1:1 | 0.5 | 0.17 |
| penflufen:propiconazole 4:6 | 0.5 | 0.17 |
| penflufen:propiconazole 3:7 | 0.3 | 0.10 |
| penflufen:propiconazole 2:8 | 0.5 | 0.17 |
| penflufen:propiconazole 1:9 | 0.5 | 0.17 |
| propiconazole | 3.0 | — |

2.6 Combinations of Penflufen and Permethrin against the Wood-destroying Organism *Poria placenta*

|  | MIC against Poria placenta (ppm) | SI |
|---|---|---|
| penflufen | 0.1 | — |
| penflufen:permethrin 7:3 | 0.1 | 0.70 |
| penflufen:permethrin 6:4 | 0.1 | 0.60 |
| penflufen:permethrin 1:1 | 0.1 | 0.50 |
| penflufen:permethrin 4:6 | 0.1 | 0.40 |
| permethrin | >100 | — |

2.7 Combinations of Penflufen and Etofenprox against the Wood-destroying Organism *Poria placenta*

|  | MIC against Poria placenta (ppm) | SI |
|---|---|---|
| penflufen | 0.1 | — |
| penflufen:etofenprox 7:3 | 0.1 | 0.70 |
| penflufen:etofenprox 6:4 | 0.1 | 0.60 |
| penflufen:etofenprox 1:1 | 0.1 | 0.50 |
| penflufen:etofenprox 4:6 | 0.1 | 0.40 |
| penflufen:etofenprox 3:7 | 0.1 | 0.30 |
| penflufen:etofenprox 2:8 | 0.3 | 0.60 |
| penflufen:etofenprox 1:9 | 0.1 | 0.10 |
| etofenprox | >100 | — |

2.8 Combinations of Penflufen and Prochloraz against the Wood-destroying Organisms *Coniophora puteana* and *Lentinus tigrinus*

|  |  | MIC (ppm) | | SI | |
|---|---|---|---|---|---|
|  |  | Coniophora puteana | Lentinus tigrinus | Coniophora puteana | Coniophora puteana |
| penflufen |  | 3.0 | 0.3 |  |  |
| penflufen:prochloraz | 3:7 | 0.3 | 0.5 | 0.04 | 0.52 |
| penflufen:prochloraz | 2:8 | 0.3 | 1.0 | 0.03 | 0.71 |
| penflufen:prochloraz | 1:9 | 1.0 | 1.0 | 0.06 | 0.38 |
| prochloraz |  | >30 | 20 |  |  |

2.9 Combinations of Penflufen and Bifenthrin against the Wood-destroying Organism *Coriolus versicolor*

|  | MIC against *Coriolus versicolor* (ppm) | SI |
|---|---|---|
| penflufen | 0.1 | — |
| penflufen:bifenthrin 4:6 | 0.1 | 0.40 |
| penflufen:bifenthrin 3:7 | 0.1 | 0.30 |
| penflufen:bifenthrin 2:8 | 0.3 | 0.60 |
| penflufen:bifenthrin 1:9 | 0.1 | 0.10 |
| bifenthrin | 60.0 | — |

2.10 Combinations of Penflufen and Cypermethrin against the Wood-destroying Organisms *Coriolus versicolor* and *Poria placenta*

|  |  | MIC (ppm) | | SI | |
|---|---|---|---|---|---|
|  |  | *Coriolus versicolo* | *Poria placenta* | *Coriolus versicolor* | *Poria placenta* |
| penflufen |  | 0.1 | 0.1 |  |  |
| penflufen:cypermethrin | 7:3 | 0.1 | 0.1 | 0.70 | 0.70 |
| penflufen:cypermethrin | 6:4 | 0.1 | 0.1 | 0.60 | 0.60 |
| penflufen:cypermethrin | 1:1 | 0.1 | 0.1 | 0.50 | 0.50 |
| penflufen:cypermethrin | 4:6 | 0.1 | 0.1 | 0.40 | 0.40 |
| penflufen:cypermethrin | 3:7 | 0.1 | 0.1 | 0.30 | 0.30 |
| penflufen:cypermethrin | 2:8 | 0.3 | 0.3 | 0.60 | 0.60 |
| penflufen:cypermethrin | 1:9 | 0.1 | 0.5 | 0.10 | 0.50 |
| cypermethrin |  | >100 | >100 |  |  |

Example 3

Activity Test Analogously to EN113

Penflufen (I) was tested analogously to the EN113 standard test for activity against wood-destroying fungi. In contrast to the standard test, smaller pieces of wood were used and the pieces of wood were exposed to attack by the fungi for a shorter period of time.

To this end, dried test specimen (25×15×4 mm) made of pine (*Pinus sylvestris*) were in each case vacuum-drenched with solutions of penflufen (I) in toluene. From the concentration of penflufen (I) in the drench solution and the uptake of the drench solution into the test specimen, the amount of active compound taken up by the test specimen (retention) was calculated. The test specimens were dried and then weighed. To prevent falsifying colonisation by foreign pathogens, the test specimen were sterilised with γ rays.

3.1 Activity against *Poria placenta*

The test specimen were brought into contact with the wood-destroying organism *Poria placenta* and stored for 6 weeks. The test pieces of wood were then cleaned, dried and weighed. This was used to calculate the loss of mass. For each retention, the mean of 6 test specimens was determined.

| No. | Retention of penflufen [g/m$^3$] | Loss of mass [%] |
|---|---|---|
| 1 | 0 | 20 |
| 2 | 50 | 0 |
| 3 | 102 | 0 |

Penflufen (I) shows very good activity against the wood-destroying fungus *Poria placenta*.

3.2 Activity against *Coniophora puteana*

The test specimens were brought into contact with the wood-destroying organism *Coniophora puteana* and stored for 6 weeks. The test pieces of wood were then cleaned, dried and weighed. This was used to calculate the loss of mass. For each retention, the mean of 6 test specimens was determined.

| No. | Retention of penflufen [g/m$^3$] | Loss of mass [%] |
|---|---|---|
| 1 | 0 | 24 |
| 2 | 50 | 0 |
| 3 | 103 | 0 |

Penflufen (I) shows very good activity against the wood-destroying fungus *Coniophora puteana*.

What is claimed is:

1. A process for protecting wood and wood-comprising materials against attack or destruction by wood-destroying basidiomycetes, the process comprising treating a wood or wood-comprising material with a treatment solution comprising at least one diluent or solvent, and 0.001% to 5% by weight biocidal compounds comprising 65-55% by weight of at least one of penflufen and salts thereof, and 35-45% by weight of copper oxide, and the treatment solution has an efficacy of greater than 99% against wood destroying basidiomycetes.

2. The process according to claim 1 wherein:
    the basidiomycetes comprise holobasidiomycetes; and
    the treating comprises treating the wood or wood-comprising material by at least one of painting, spraying, drenching, submersion, and impregnation of the wood or wood-comprising material with the treatment solution.

* * * * *